(12) United States Patent
Chen et al.

(10) Patent No.: US 10,070,864 B2
(45) Date of Patent: Sep. 11, 2018

(54) LOADING UNIT ASSEMBLY AND LINEAR SURGICAL STAPLER WITH LOADING UNIT ASSEMBLY

(71) Applicant: TOUCHSTONE INTERNATIONAL MEDICAL SCIENCE CO., LTD., Jiangsu (CN)

(72) Inventors: Wangdong Chen, Jiangsu (CN); Tuo Shu, Jiangsu (CN); Kaifen Fu, Jiangsu (CN); Yanping Ye, Jiangsu (CN); Yongwang Pei, Jiangsu (CN)

(73) Assignee: TOUCHSTONE INTERNATIONAL MEDICAL SCIENCE CO., LTD., Jiangsu (CN)

( * ) Notice: Subject to any disclaimer, the term of this patent is extended or adjusted under 35 U.S.C. 154(b) by 518 days.

(21) Appl. No.: 14/743,641

(22) Filed: Jun. 18, 2015

(65) Prior Publication Data
US 2015/0282807 A1    Oct. 8, 2015

Related U.S. Application Data

(63) Continuation of application No. PCT/CN2013/088941, filed on Dec. 10, 2013.

(30) Foreign Application Priority Data

Dec. 18, 2012 (CN) .......................... 2012 1 0595223

(51) Int. Cl.
| | |
|---|---|
| A61B 17/10 | (2006.01) |
| A61B 17/072 | (2006.01) |
| A61B 17/068 | (2006.01) |
| A61B 17/32 | (2006.01) |
| A61B 17/00 | (2006.01) |
| A61B 90/00 | (2016.01) |

(52) U.S. Cl.
CPC .......... *A61B 17/105* (2013.01); *A61B 17/068* (2013.01); *A61B 17/07207* (2013.01); *A61B 17/320016* (2013.01); *A61B 2017/00473* (2013.01); *A61B 2090/038* (2016.02)

(58) Field of Classification Search
CPC ............ A61B 17/105; A61B 17/07207; A61B 17/320016
USPC .......................... 227/180.1, 176.1, 175.1, 19
See application file for complete search history.

(56) References Cited

U.S. PATENT DOCUMENTS

| | | | |
|---|---|---|---|
| 5,782,396 A * | 7/1998 | Mastri | A61B 17/07207 227/175.3 |
| 7,753,246 B2 | 7/2010 | Scirica | |

FOREIGN PATENT DOCUMENTS

| | | |
|---|---|---|
| CN | 101797174 A | 8/2010 |
| CN | 101856251 A | 10/2010 |

(Continued)

*Primary Examiner* — Nathaniel Chukwurah
(74) *Attorney, Agent, or Firm* — Seed IP Law Group LLP

(57) ABSTRACT

A loading unit assembly used for a linear surgical stapler, which includes a staple cartridge frame and a knife driver beam. The knife driver beam has a movable safety block defined on a surface of a proximal end thereof, and a protrusion is correspondingly defined on the staple cartridge frame. When the loading unit assembly is at its initial position, a front surface at a distal end of the safety block engages with the protrusion to stop a movement of the knife driver beam and the safety block. When the loading unit assembly is at its working position, the safety block is relatively separated from the protrusion.

15 Claims, 7 Drawing Sheets

(56) References Cited

FOREIGN PATENT DOCUMENTS

| | | |
|---|---|---|
| CN | 202122595 U | 1/2012 |
| CN | 202409017 U | 9/2012 |
| CN | 202982105 U | 6/2013 |
| CN | 203074789 U | 7/2013 |
| EP | 2 133 029 A1 | 12/2009 |

* cited by examiner

LOADING UNIT ASSEMBLY AND LINEAR SURGICAL STAPLER WITH LOADING UNIT ASSEMBLY

TECHNICAL FIELD

The present application relates to a loading unit assembly and linear surgical stapler with loading unit assembly, which belongs to the technical field of medical instruments.

BACKGROUND

Linear surgical staplers are widely used in surgical operations for wound closure, and internal tissue closure and excision. With the development of the surgical operation, now, people have been more and more inclined to minimally invasive operation. Broadly speaking, a surgery which reduces trauma can be known as minimally invasive operation. While, generally speaking, the minimally invasive surgery is referring to the endoscopic operation in a narrow sense. For the endoscopic surgery, generally, a doctor only needs to open a few of holes and puts surgical staplers used for excision and anastomosis of tissues and auxiliary equipment into the patient's body for surgery through the holes. The trauma of minimally invasive operation brings to the patient is very small and the patient can recover in a short period of time. Therefore, the minimally invasive operation has been paid more and more attention.

U.S. Pat. No. 7,753,246 discloses a linear surgical stapler used in minimally invasive operation, which includes a body portion, and the body portion includes a shell and a firing handle pivotally arranged on the shell, the shell having a relatively movable firing ejector rod therein, the firing ejector rod being able to push the loading unit assembly which located at the front end of the shell to carry out anastomosis and excision. Specifically, the loading unit assembly includes a staple cartridge frame and an anvil pivotally connected with the staple cartridge frame. The staple cartridge frame includes a detachable staple cartridge which includes a series of staple retention holes, generally 4 or 6 rows, accommodating staple pushers and staples. The anvil is arranged with staple forming grooves corresponding to the staple retention holes. The loading unit assembly further includes a movable driver beam arranged in a housing of the loading unit assembly. The driver beam has a knife at the distal end thereof to close the staple cartridge and the anvil when the driver beam is advanced. The knife has a knife blade arranged on its distal central to sever tissues clamped between the staple cartridge and the anvil as the driver beam is advanced. Two wedges are arranged abutting opposite side of the knife blade, that when the knife is advanced, the knife actuates the wedges to push the staple pushers out of the staple cartridge, and the staple pushers sequentially eject staples from the staple cartridge to staple tissues clamped between the cartridge and the anvil.

In the prior art, the loading unit assembly is replaceable from the body portion. When the loading unit assembly assembled on the body portion, the housing of loading unit assembly is inserted into an outer tube distant the staple cartridge. Meanwhile, a lug defined at a proximal end of the driver beam receives in a receiving space located on a distal end of the firing ejector rod; then the loading unit assembly is rotated to engage the housing and tube together and axially fix the driver beam and the firing ejector rod together. After the loading unit assembly fixed to the body portion, a firing of loading unit assembly can be processed subsequently.

After the assembly of the surgical stapler, usually, it needs a long-distance transportation to other places. In the transport process, it is possible that the surgical stapler is shaked or impacted and results in the firing ejector rod is advanced and the staples are fired. Or, after firing of the surgical stapler for the first time, doctors need to replace the loading unit assembly. If the doctor is lack of experience, the loading unit assembly may not be fully installed in place. In the above two cases, if the doctor fires the surgical stapler, that will lead to a serious damage to the surgical stapler, or even cause a medical accident.

SUMMARY

In an embodiment, a loading unit assembly facilitates preventing activation of the loading unit assembly if loading unit assembly is not be fully installed in place. In an embodiment, and a linear surgical stapler includes the loading unit assembly.

In an embodiment, a linear surgical stapler includes: a loading unit assembly and a body engaged with the loading unit assembly. In an embodiment, the loading unit assembly has a staple cartridge frame and an anvil pivotally connected with the staple cartridge frame. In an embodiment, a housing is arranged at a proximal end of the loading unit assembly. The housing receives a movable knife driver beam therein. The knife driver beam defines a knife at a distal end thereof. In an embodiment, the body has a tube arranged at a distal end thereof to detachably connect with the housing, and a firing ejector rod is movably received in the tube and selectively engaging with the knife driver beam. In an embodiment, the knife driver beam has a movable safety block defined on a surface of a proximal end thereof, and a protrusion is correspondingly defined on the staple cartridge frame.

In an embodiment, when the loading unit assembly is at its initial position, the housing and tube are not relatively fixed, and the safety block engages with the protrusion to stop a movement of the knife driver beam and the safety block. In an embodiment, when the loading unit assembly is at its working position, the housing and tube are relatively fixed, and the safety block is relatively separated from the protrusion.

In an embodiment, when the loading unit assembly is at its working position, an axial plane that the safety block arranged thereon is parallel to another axial plane that the protrusion arranged thereon in a direction of the movement of the knife driver beam.

In an embodiment, at least one spring is provided. One end of the spring abuts against a side of the safety block, while another end of the spring abuts against a side of the staple cartridge frame.

In an embodiment, the safety block defines at least one through hole. The knife driver beam has at least one pin extending through the through hole. In an embodiment, the spring surrounds an outer side of the pin.

In an embodiment, the knife driver beam has a claw portion at a proximal end thereof, and the firing ejector rod defines a through opening slot at a distal end thereof. The knife driver beam and the firing ejector rod are axially fixed together via the engagement of claw portion and the opening slot.

In an embodiment, a cross section at the distal end of the firing ejector rod is "I" shape with a notch defined therein. When the claw portion of the knife driver beam extends into the firing ejector rod, the safety block is located in the notch; when the firing ejector rod is rotated relative to the knife driver beam, an actuating face actuates the safety block away from the knife driver beam.

In an embodiment, a loading unit assembly, includes a staple cartridge frame and an anvil pivotally connected with staple cartridge frame. A housing is arranged at a proximal end of the loading unit assembly. The housing receives a movable knife driver beam therein. The knife driver beam defines a knife at a distal end thereof. The knife driver beam has a safety block defined on a surface of a proximal end thereof. A protrusion is correspondingly defined on the staple cartridge frame and has an engagement with the knife driver beam. The safety block and the knife driver beam is relatively stationary to each other in a axial direction of the knife driver beam. The safety block defines a first position and a second position in a radial direction of the knife driver beam. When the safety block is at its first position, the safety block contacts with the protrusion to stop a move of the knife driver beam in an axial direction thereof. When the safety block is at its second position, the safety block is relatively separated from the protrusion.

In an embodiment, when the safety block at its second position, an axial plane that the safety block arranged thereon is parallel to another axial plane that the protrusion arranged thereon in a direction of the movement of the knife driver beam.

In an embodiment, at least one spring is provided. One end of the spring abuts against a side of the safety block, while another end of the spring abuts against a side of the staple cartridge frame.

In an embodiment, the safety block defines at least one through hole. The knife driver beam has at least one pin extending through the through hole.

In an embodiment, the spring surrounds an outer side of the pin.

In an embodiment, the knife driver beam has a claw portion at a proximal end thereof.

One or more embodiments may facilitate: providing a safety member in the loading unit assembly, to prevent a mistake firing of the loading unit assembly when the firing ejector rod moves forwardly if the loading unit assembly is not fully assemble to its place or the loading unit assembly is forced by an outer force in a long-distance transportation. One or more embodiments may comprise a structure which is simple, effective and very practical.

ILLUSTRATED EMBODIMENTS

Embodiment 1

Figure 1:
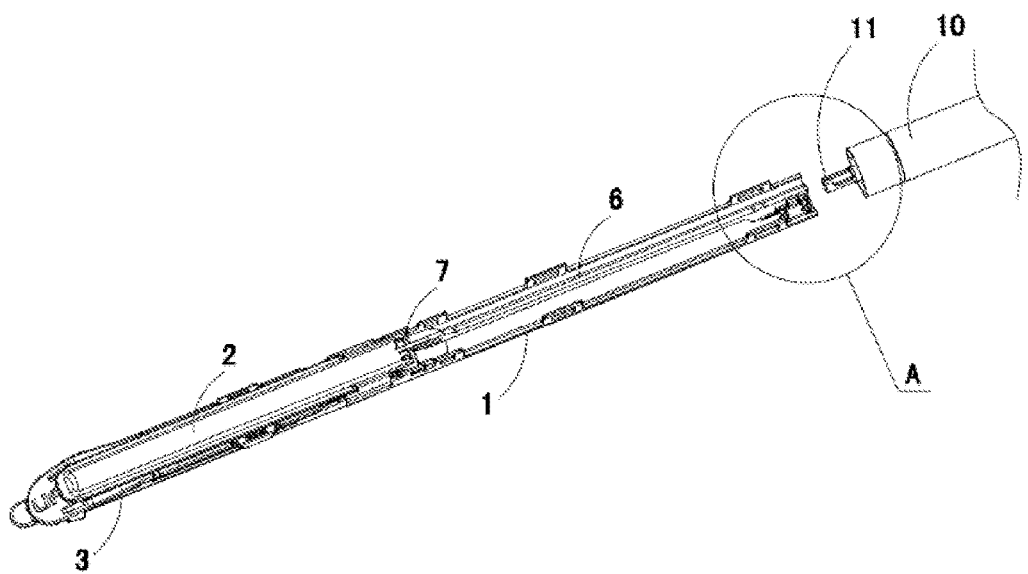
FIG. 1 is a perspective view of a loading unit assembly in accordance with an illustrated embodiment of the present application, wherein the housing is not shown.

Referring to FIG. 1, the present application discloses a linear surgical stapler used in minimally invasive operation. In accordance with the prior art, the linear surgical stapler includes a shell, a tube 10 arranged at a distal end of the shell and detachably fixed with a housing, and a firing ejector rod 11 movably received in the tube 10 and selectively engaging with a knife driver beam 6. At the distal end of the tube 10, a loading unit assembly of the linear surgical stapler is provided detachably.

Figure 2:
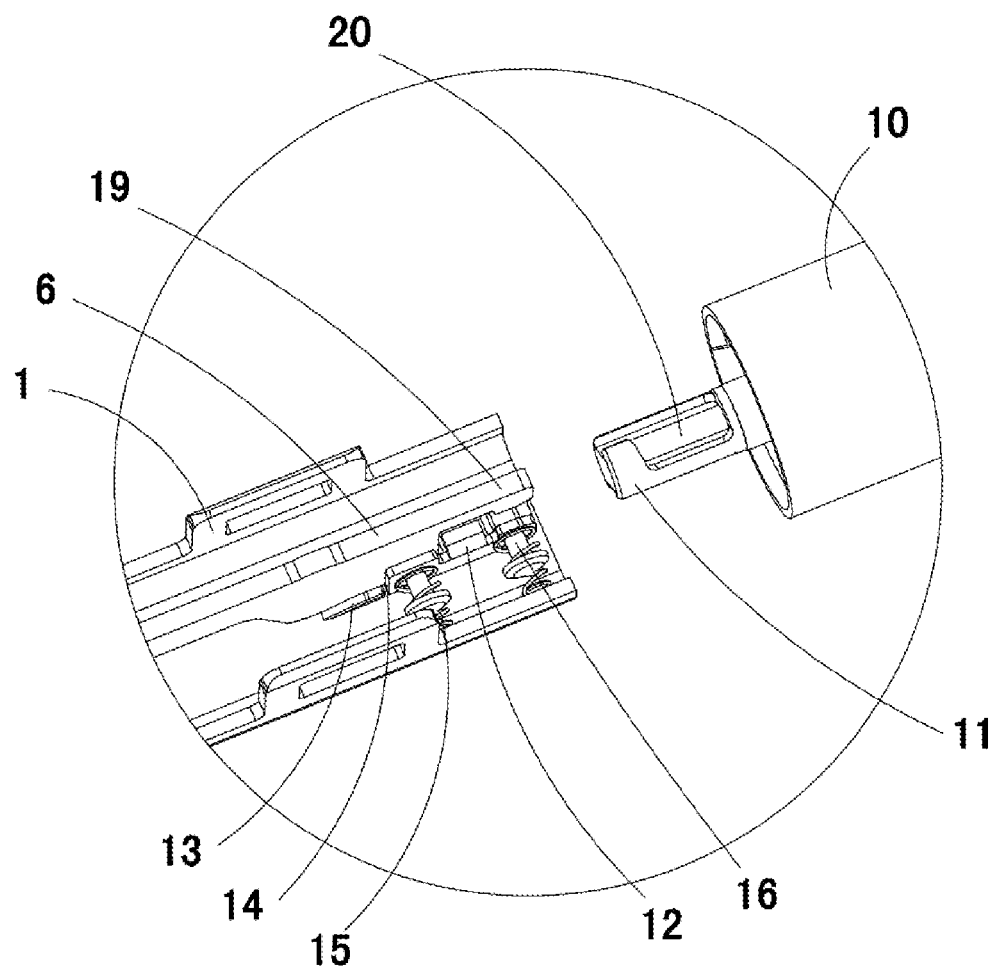
FIG. 2 an enlarged view of structures in the circle A as shown in FIG. 1.

Referring to FIGS. 1 and 2, the loading unit assembly of the linear surgical stapler includes: a staple cartridge frame 1 located at a distal end thereof and an anvil 2 pivotally connected with staple cartridge frame 1. The staple cartridge frame 1 includes a detachable staple cartridge 3 which including a series of staple retention holes to accommodate staple pushers and staples. A housing (not shown) is at a proximal end thereof, the housing receives the knife driver beam 6 movably therein; the knife driver beam 6 defining a knife at a distal end thereof, both upper and below portion of the knife defining a protrusion and the knife is a I shape knife 7. In a advancement process of the I shape knife 7, it presses the expanded tissues to make the tissues thin and uniform, and further, the I shape knife 7 close the staple cartridge 3 and the anvil 2. The I shape knife 7 has a knife blade arranged on its distal central, to sever tissue clamped between the staple cartridge 3 and the anvil 2 as the I shape knife 7 is advanced. Two wedges are arranged abutting opposite side of the knife blade, so that when the I shape knife 7 is advanced, the I shape knife 7 actuates the wedges to push the staple pushers out of the staple cartridge 3, and further the staple pushers sequentially eject staples from the staple cartridge 3 to staple tissues clamped between the staple cartridge 3 and the anvil 2.

The housing and tube 10 are relatively fixed or relatively separated from each other. When the loading unit assembly is at its initial position, the housing and tube 10 are not relatively fixed; when the loading unit assembly is at its working position, the housing and tube 10 are relatively fixed, and the knife driver beam 6 is axially fixed with the firing ejector rod 11 axially. Specifically, the knife driver beam 6 has a claw portion 19 at a proximal end thereof, and the firing ejector rod 11 defines a through opening slot 20 at a distal end thereof, the knife driver beam 6 and the firing ejector rod 11 being axially fixed together via the engagement of claw portion 19 and the opening slot 20. Of course, an axial match tolerance is allowable between the knife driver beam 6 and the firing ejector rod 11, leading to a slightly relative displacement between the knife driver beam 6 and the firing ejector rod 11.

The knife driver beam 6 has a movable safety block 12 defined on a surface of a proximal end thereof, and a protrusion 13 is correspondingly defined on the staple cartridge frame 1. The safety block 12 is a flake structure. A first surface of the safety block 12 is connected with two springs 15, and the other end of the spring 15 is connected with the staple cartridge frame 1. With this arrangement, when the loading unit assembly is at its initial position, the acting force of the spring 15 is acting on the first side of the safety block 12, making a second side of the safety block 12 close to a proximal side of the knife driver beam 6. The safety block 12 is provided with two through holes, wherein the knife driver beam 6 is fixed with two pins 16, and the pins 16 pass through the corresponding through holes. The spring 15 surrounds an outer side of the pin 16.

Figure 3:
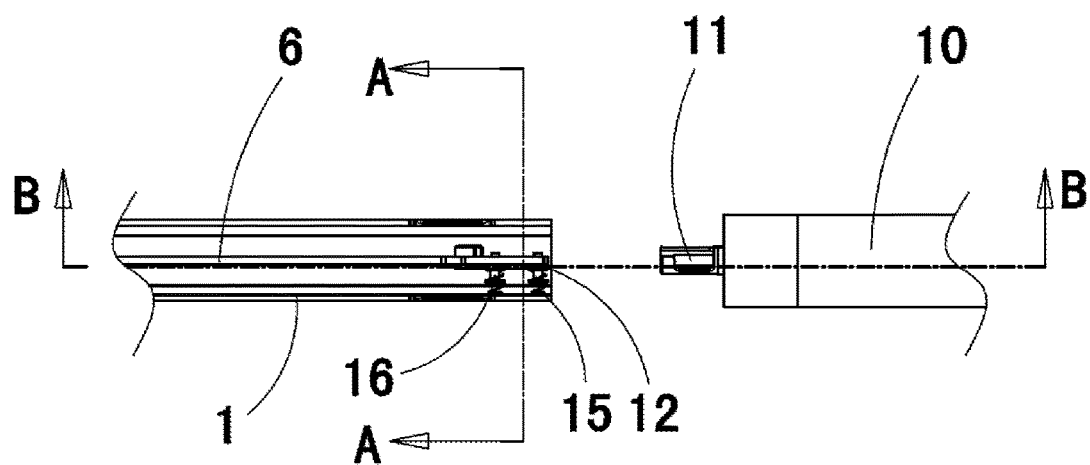
FIG. 3 is a front plan view of the loading unit assembly when it is in its initial position.
Figure 4:
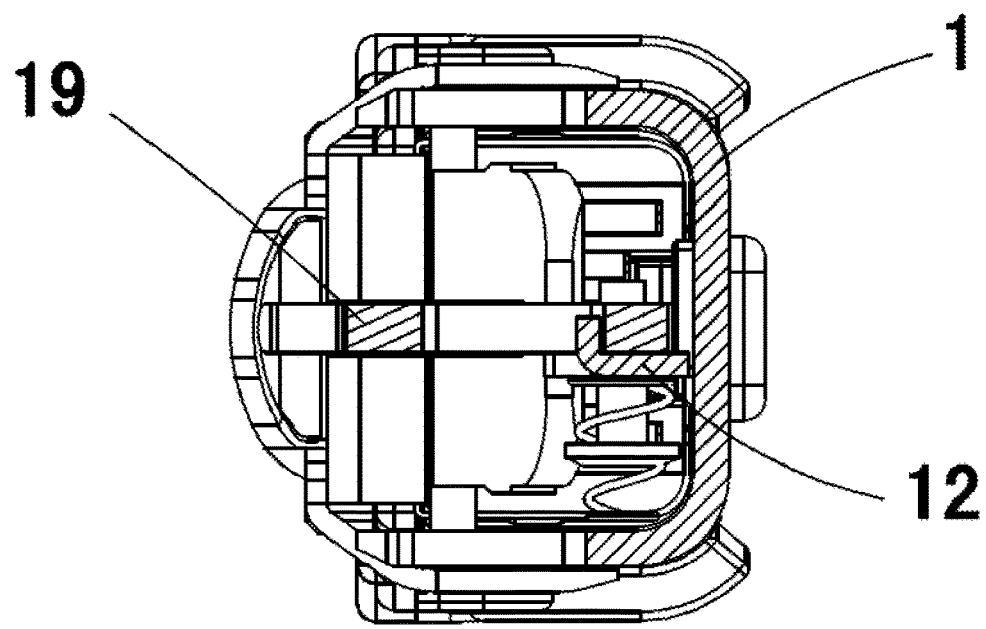
FIG. 4 is an enlarged cross-sectional view taken along a line A-A in FIG. 3.
Figure 5:
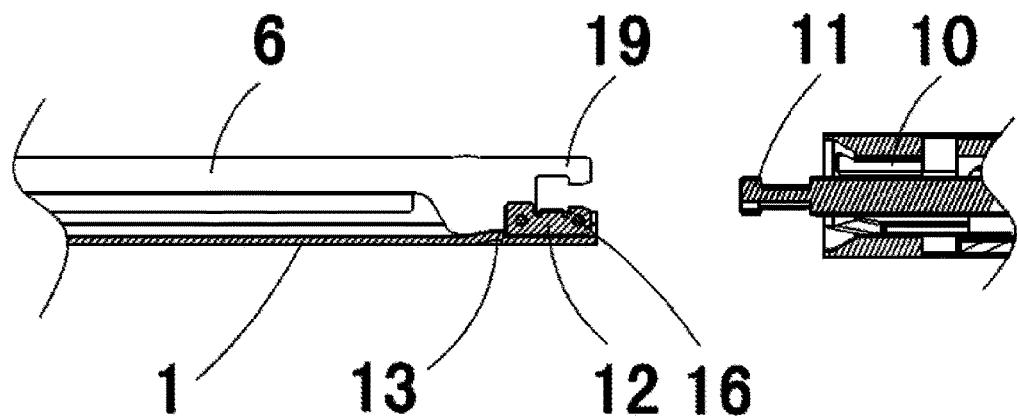
FIG. 5 is a cross-sectional view taken along a line B-B in FIG. 3.

Referring to FIGS. 3-5, when the loading unit assembly is at the initial position, the housing and the tube 10 are not relatively fixed. Under this position, a front surface 14 located at a distal end of the safety block 12 abuts against the protrusion 13 and limits a movement of the knife driver beam 6 and the safety block 12.

Figure 6:
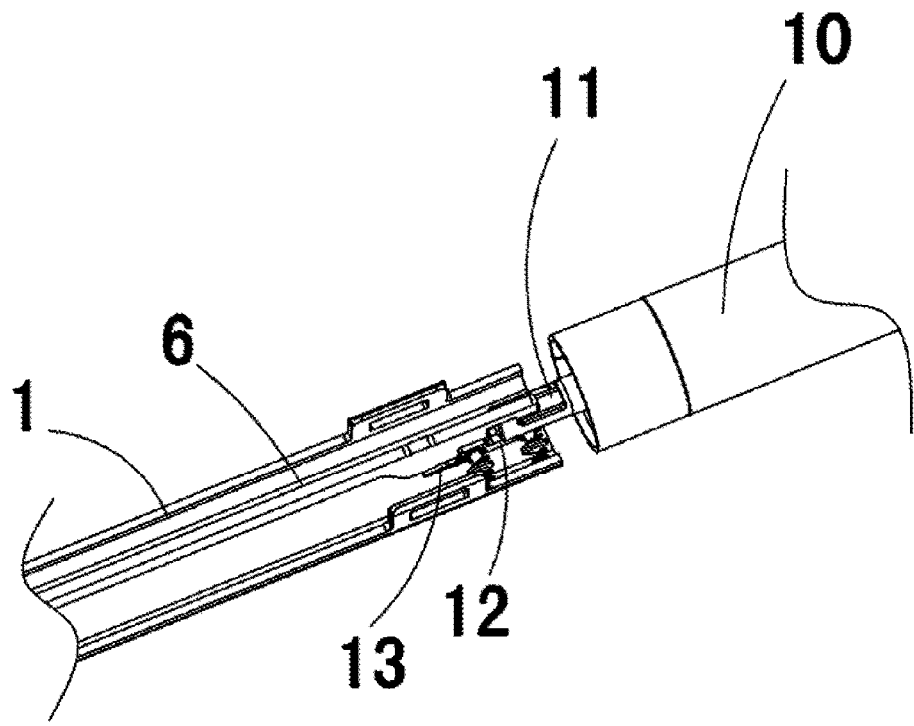
FIG. 6 is a perspective view of the loading unit assembly in accordance with the illustrated embodiment when it is at its intermediate status.
Figure 7:
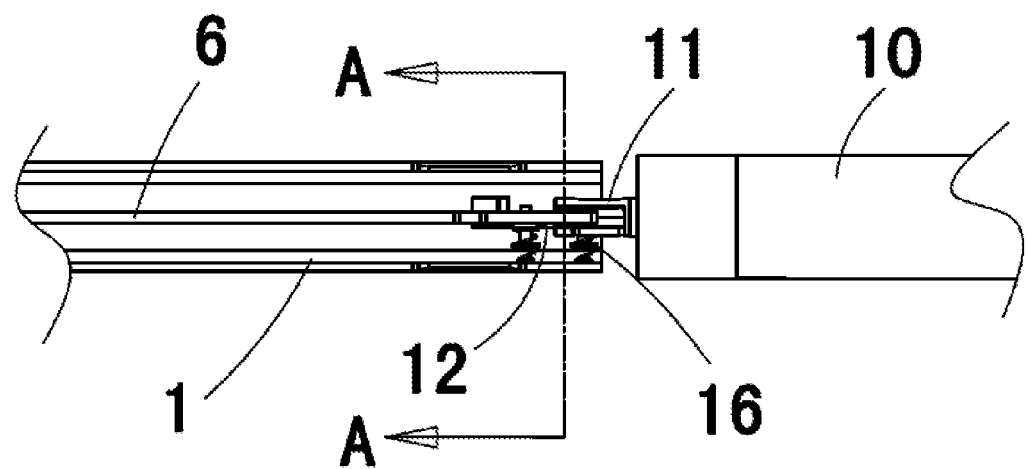
FIG. 7 is a front plan view of the loading unit assembly in accordance with the illustrated embodiment when it is at its intermediate status.
Figure 8:
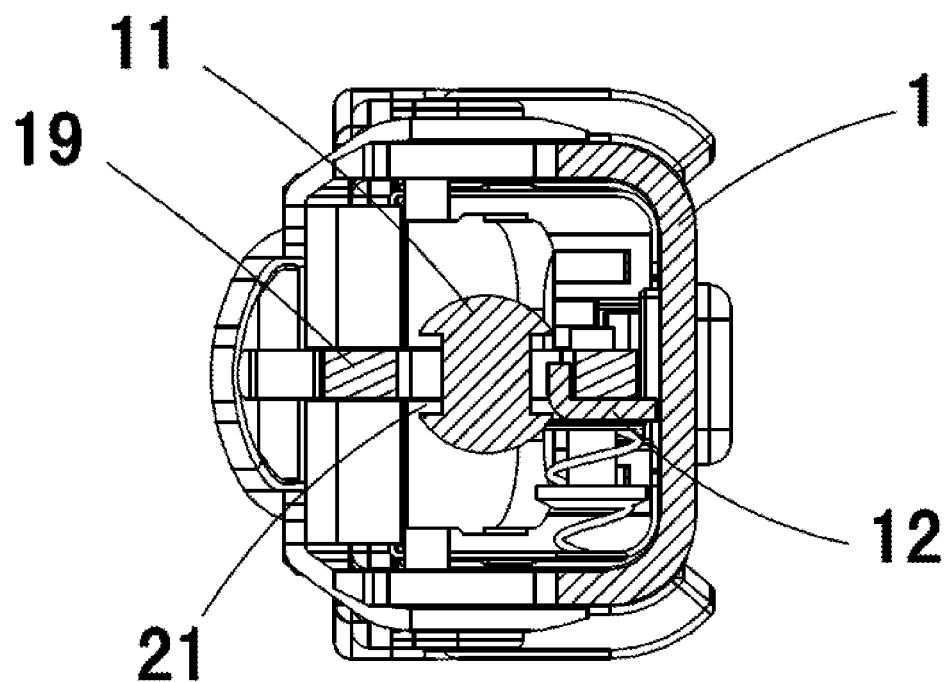
FIG. 8 an enlarged cross-sectional view taken along a line A-A in FIG. 7.
Figure 9:
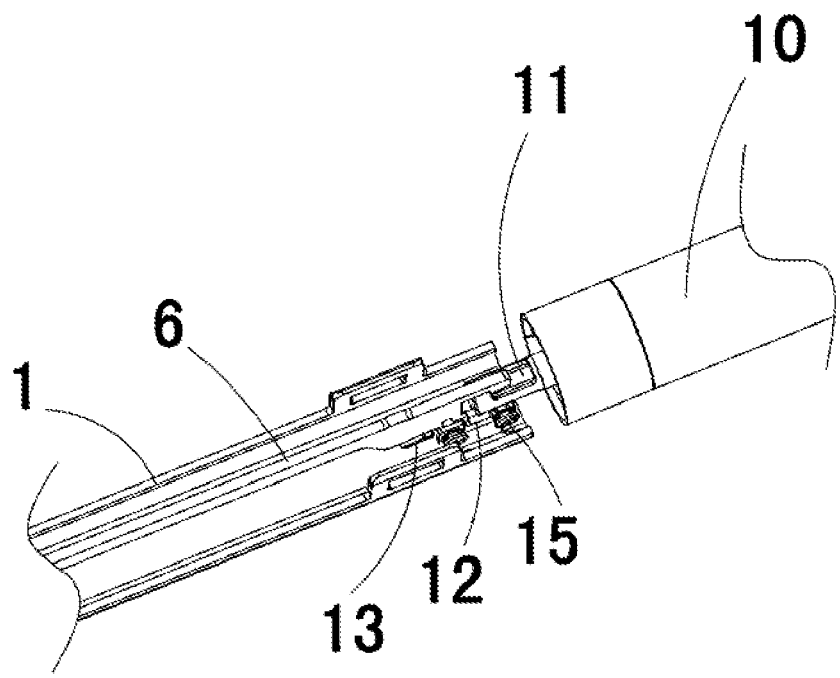
FIG. 9 is a perspective view of the loading unit assembly in accordance with the illustrated embodiment when it is at its working status.
Figure 10:
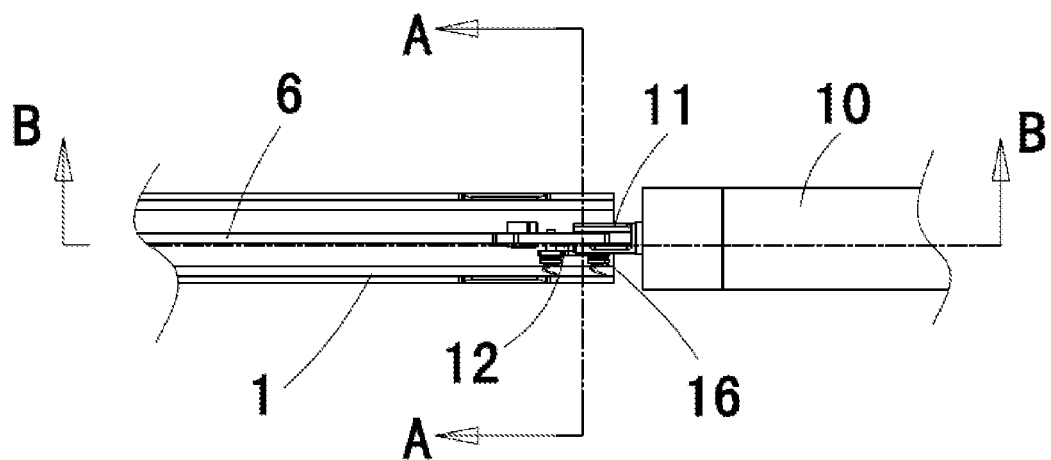
FIG. 10 is a front plan view of the loading unit assembly in accordance with the illustrated embodiment when it is at its working status.
Figure 11:
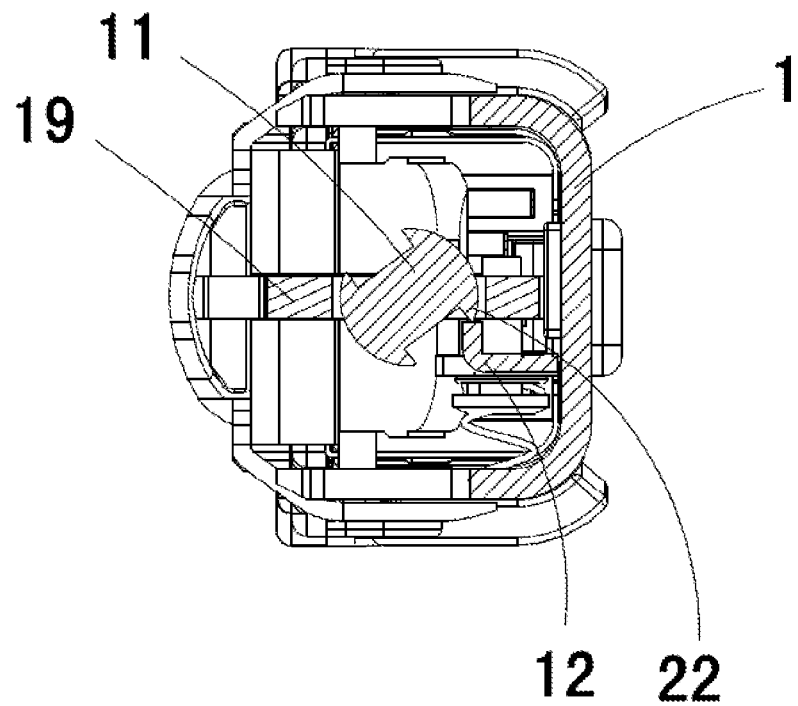
FIG. 11 is an enlarged cross-sectional view taken along a line A-A in FIG. 10.
Figure 12:
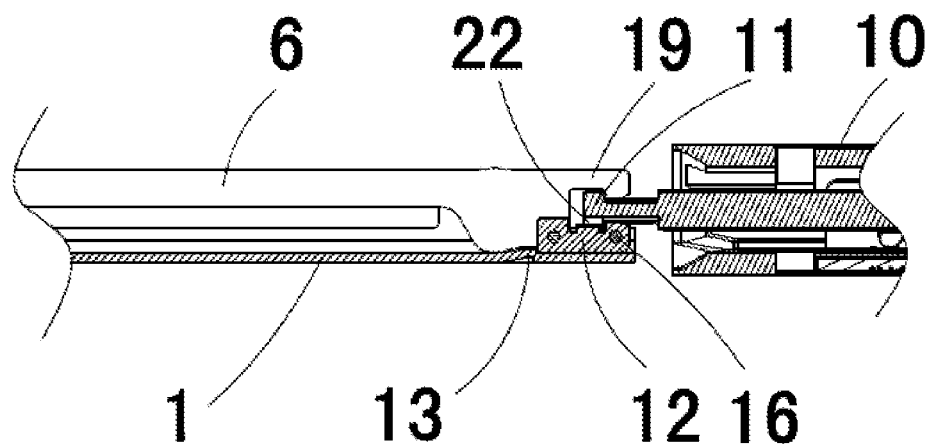
FIG. 12 is an enlarged cross-sectional view taken along a line B-B in FIG. 10.

A cross section at the distal end of the firing ejector rod 11 is in an "I" shape with a notch (21) defined therein. When the loading unit assembly is at its intermediate status as shown in the FIGS. 6-8, the housing is just inserted into the tube 10, that is when the claw portion 19 of the knife driver beam 6 extends into the firing ejector rod 11, the safety block 12 is located in the notch 21. Now, under this status, there is no relative displacement between the knife driver beam 6 and the safety block 12.

Referring to FIGS. 9-12, when the loading unit assembly is at its working position, the knife driver beam 6 and the firing ejector rod 11 are axially fixed together fully, thus the claw portion 19 is axially fixed with the opening slot 20 via a rotation of the housing. Under this position, the knife driver beam 6 rotates relative to the firing ejector rod 11. At this time, an "I" shaped actuating face 22 of the firing ejector rod 11 actuates the safety block 12 to overcome the acting force of the springs 15 and to be away from the knife driver beam 6. In a direction of the movement of the knife driver beam 6, an axial plane that the safety block 12 arranged thereon is parallel to another axial plane that the protrusion 13 arranged thereon, to make the front surface 14 located at a distal end of the safety block 12 being relatively apart from the protrusion 13. Since a distance between the safety block 12 and the knife driver beam 6 is greater than a thickness of the protrusion 13, that the safety block 12 and the knife driver beam 6 can escape from the limitation of the protrusion 13 and can move along the axis of the staple cartridge frame 1.

When replacing the loading unit assembly, rotate the housing in a reverse direction, then the loading unit assembly detaches form the tube 10. And meanwhile, the knife driver beam 6 is separated from the firing ejector rod 11. At this time, under an acting force of the springs 15, the safety block 12 resets to limit a movement of the knife driver beam 6 again.

In the present description, the words describing position and direction are all based on the instrument operator as a reference. The proximal end refers to the end close to the operator and the distal end refers to the end far from the operator.

The present application discloses a variety of embodiments. For example, if the protrusion 13 is defined on the housing, under a cooperation of the safety block 12, this arrangement also can play a safety role. Embodiments may be formed by the equivalent variation or the equivalent modification of disclosed embodiments.

What is claimed is:

1. A linear surgical stapler, comprising:
    a loading unit assembly and a body engaged with the loading unit assembly, the loading unit assembly comprising a staple cartridge frame and an anvil pivotally connected with the staple cartridge frame; and
    a housing arranged at a proximal end of the loading unit assembly, the housing receiving a movable knife driver beam therein;
    the knife driver beam defining a knife at a distal end thereof;
    the body having a tube arranged at a distal end thereof to detachably connect with the housing, and a firing ejector rod movably received in the tube and selectively engaging with the knife driver beam;
    wherein:
    the knife driver beam has a movable safety block defined on a surface of a proximal end thereof, and a protrusion is correspondingly defined on the staple cartridge frame;
    when the loading unit assembly is at its initial position, the housing and tube are not relatively fixed, and the safety block engages with the protrusion to stop a movement of the knife driver beam and the safety block;
    when the loading unit assembly is at its working position, the housing and tube are relatively fixed, and the safety block is relatively separated from the protrusion.

2. The linear surgical stapler as claimed in claim 1, wherein when the loading unit assembly is at its working position, an axial plane that the safety block arranged thereon is parallel to another axial plane that the protrusion arranged thereon in a direction of the movement of the knife driver beam.

3. The linear surgical stapler as claimed in claim 1, comprising at least one spring, one end of the spring abutting against a side of the safety block, another end of the spring abutting against a side of the staple cartridge frame.

4. The linear surgical stapler as claimed in claim 3, wherein the safety block defines at least one through hole, and the knife driver beam has at least one pin extending through the through hole.

5. The linear surgical stapler as claimed in claim 4, wherein the spring surrounds an outer side of the pin.

6. The linear surgical stapler as claimed in claim 1, wherein the knife driver beam has a claw portion at a proximal end thereof, and the firing ejector rod defines a through opening slot at a distal end thereof, the knife driver beam and the firing ejector rod being axially fixed together via the engagement of claw portion and the opening slot.

7. The linear surgical stapler as claimed in claim 6, wherein a cross section at the distal end of the firing ejector rod is in an "I" shape with a notch defined therein, when the claw portion of the knife driver beam extends into the firing ejector rod, the safety block is located in the notch; when the firing ejector rod is rotated relative to the knife driver beam, an actuating face actuates the safety block away from the knife driver beam.

8. The linear surgical stapler of claim 1 wherein, when the loading unit assembly is in the initial position, the safety block abuts against the protrusion to stop movement of the knife driver beam and the safety block.

9. A loading unit assembly, comprising:
    a staple cartridge frame and an anvil pivotally connected with staple cartridge frame, and a housing arranged at a proximal end of the loading unit assembly, the housing receives a movable knife driver beam therein;
    the knife driver beam defines a knife at a distal end thereof; characteristic in that: the knife driver beam has a safety block defined on a surface of a proximal end thereof, and a protrusion is correspondingly defined on the staple cartridge frame and has an engagement with the knife driver beam, the safety block and the knife driver beam are relatively stationary to each other in an axial direction of the knife driver beam, the safety block defines a first position and a second position in a radial direction of the knife driver beam, when the safety block is at its first position, the safety block contacts with the protrusion to stop a movement of the knife driver beam in its axial direction; when the safety block is at its second position, the safety block is relatively separated from the protrusion.

10. The loading unit assembly as claimed in claim 9, wherein when the safety block is at its second position, an axial plane that the safety block arranged thereon is parallel to another axial plane that the protrusion arranged thereon in a direction of the movement of the knife driver beam.

11. The loading unit assembly as claimed in claim 9, comprising at least one spring, one end of the spring abutting against a side of the safety block, another end of the spring abutting against a side of the staple cartridge frame.

12. The loading unit assembly as claimed in claim 11, wherein the safety block defines at least one through hole, and the knife driver beam has at least one pin extending through the through hole.

13. The loading unit assembly as claimed in claim 12, wherein the spring surrounds an outer side of the pin.

14. The loading unit assembly as claimed in claim 9, wherein the knife driver beam has a claw portion at a proximal end thereof.

15. The loading unit assembly of claim 9 wherein, in the first position, the safety block abuts against the protrusion to stop movement of the knife driver beam in the axial direction.

* * * * *